(12) United States Patent
Markiewicz et al.

(10) Patent No.: US 9,290,521 B2
(45) Date of Patent: Mar. 22, 2016

(54) METHOD FOR PROTECTING HYDROXYL OR AMINE OR THIOL FUNCTIONS, NOVEL COMPOUNDS WITH PROTECTED HYDROXYL OR AMINE OR THIOL GROUPS, AS WELL NOVEL COMPOUNDS FOR THE IMPLEMENTATION OF THIS METHOD

(71) Applicants: INSTYTUT CHEMII BIOORGANICZNEJ POLSKIEJ AKADEMII NAUK, Poznań (PL); FUNDACJA UNIWERSYTETU IM. ADAMA MICKIEWICZA W POZNANIU, Poznań (PL)

(72) Inventors: Wojciech Tadeusz Markiewicz, Poznań (PL); Marcin Krzysztof Chmielewski, Poznań (PL); Sylwia Maria Musial, Kościan (PL); Hieronim Franciszek Maciejewski, Poznań (PL); Grzegorz Hreczycho, Poznań (PL)

(73) Assignees: INSTYTUT CHEMII BIOORGANICZNEJ POLSKIEJ AKADEMII NAUK, Poznan (PL); FUNDACJA UNIWERSYTETU IM. ADAMA MICKIEWICZA W POZNANIU, Poznan (PL)

( * ) Notice: Subject to any disclaimer, the term of this patent is extended or adjusted under 35 U.S.C. 154(b) by 0 days.

(21) Appl. No.: 14/396,474

(22) PCT Filed: Apr. 23, 2013

(86) PCT No.: PCT/PL2013/000058
§ 371 (c)(1),
(2) Date: Oct. 23, 2014

(87) PCT Pub. No.: WO2013/165266
PCT Pub. Date: Nov. 7, 2013

(65) Prior Publication Data
US 2015/0094462 A1 Apr. 2, 2015

(30) Foreign Application Priority Data
Apr. 27, 2012 (PL) .................................... 399003

(51) Int. Cl.
| | |
|---|---|
| C07F 7/08 | (2006.01) |
| C07F 7/12 | (2006.01) |
| C07B 51/00 | (2006.01) |
| C07F 7/10 | (2006.01) |
| C07F 7/18 | (2006.01) |
| C07H 23/00 | (2006.01) |

(52) U.S. Cl.
CPC .............. C07F 7/0834 (2013.01); C07B 51/00 (2013.01); C07F 7/0821 (2013.01); C07F 7/10 (2013.01); C07F 7/12 (2013.01); C07F 7/1868 (2013.01); C07H 23/00 (2013.01)

(58) Field of Classification Search
None
See application file for complete search history.

(56) References Cited

U.S. PATENT DOCUMENTS 4,841,083 A * 6/1989 Nagai et al. ................... 556/430
6,800,751 B2 10/2004 Sanghvi et al.

OTHER PUBLICATIONS

Markiewicz et al., "A New Type of Silyl Protecting Groups in Nucleoside Chemistry," Nucleic Acid Research, Special Publication No. 4, pp. 185-188, 1978.
Markiewicz et al., "Tetra-t-butoxydisiloxane-1,3-diyl, a New Type of Bifunctional Silyl Protective Group," Nucleic Acids Research, Symposium Series No. 18, pp. 149-152, 1987.
Wen et al., "Synthesis of 2'-O-Methoxyethylguanosine Using a Novel Silicon-Based Protecting Group," J. Org. Chem., vol. 67, pp. 7887-7889, 2002.

(Continued)

Primary Examiner — Layla Berry
(74) Attorney, Agent, or Firm — Oliff PLC

(57) ABSTRACT

A novel method of simultaneously protecting two functions which are same or different, namely hydroxyl, amine, or thiol ones, particularly in sugars, polyalcohols, nucleosides, nucleotides, peptides, and nucleic acids during an organic synthesis, and to novel compounds for implementing this method, as well as to the method of obtaining these compounds. Method of simultaneously protecting two hydroxyl, amine, or thiol functions according to the invention by carrying out a protecting reaction between a compound having at least two free hydroxyl, amine, or thiol groups, and the disilane of formula 1,

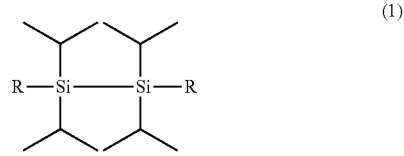

(1)

where R stands for Cl or Br, or I, or a substituent of formula 2,

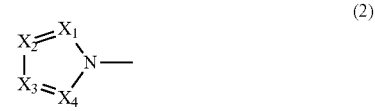

(2)

where $X_1$, $X_2$, $X_3$, $X_4$ are the same or different.

17 Claims, No Drawings

(56) References Cited

OTHER PUBLICATIONS

Corey et al., "Diisopropylsilyl Ditriflate and Di-tert-butylsilyl Ditriflate New Reagents for the Protection of Diols," Tetrahedron Letters, vol. 23, No. 47, pp. 4871-4874, 1982.
Herbal et al., "Synthesis of the Enamtiomer of Nelarabine," Tetrahedron Letters, vol. 46, pp. 2961-2964, 2005.
Clark et al., "Synthetic Methods Part (v) Protecting Groups," Ann. Rep. Prog. Chem., Section B, vol. 99, pp. 84-103, 2003.
Kako et al., "Photoinduced Electron-transfer Reaction of 7,8-Disilabicyclo[2.2.2]octa-2,5-dienes," Tetrahedron Letters, vol. 40, pp. 1133-1136, 1999.
Manfred et al., "Silicium-Verbindungen Mit Starken Intramolekularen Sterischen WechelWirkungen," Journal of Organometallic Chemistry, vol. 84, pp. 151-163, 1975.
Aug. 20, 2013 International Search Report issued in International Patent Application No. PCT/PL2013/000058.
Markiewicz, "Tetraisopropyldisiloxane-1,3-diyl, a Group for Simultaneous Protection of 3'- and 5'-Hydroxy Functions of Nucleosides," J. Chem. Research, pp. 0181-0197, 1979.

* cited by examiner

METHOD FOR PROTECTING HYDROXYL OR AMINE OR THIOL FUNCTIONS, NOVEL COMPOUNDS WITH PROTECTED HYDROXYL OR AMINE OR THIOL GROUPS, AS WELL NOVEL COMPOUNDS FOR THE IMPLEMENTATION OF THIS METHOD

The invention relates to a novel method of simultaneously protecting two functions which are same or different, namely hydroxyl, amine, or thiol ones, particularly in sugars, polyalcohols, nucleosides, nucleotides, peptides, and nucleic acids during an organic synthesis, and to novel compounds for implementing this method, as well as to the method of obtaining these compounds.

Organosilicon protecting agents are known from literature, used in organic chemistry for many years. Some of them have established a stable position in the practical chemistry of nucleic acids, nucleosides, and nucleotides.

A bifunctional protecting agent is known that effectively binds two hydroxyl groups of the ribose ring in nucleosides. 1,3-Dichloro-1,1,3,3-tetraisopropyldisiloxane, discussed for example in literature (W. T. Markiewicz, *J. Chem. Research (S)* 1979, 24-25, W. T. Markiewicz, *J. Chem. Research (M)* 1979, 19, 181-197, W. T. Markiewicz, M. Wiewiórowski, *Nucleic Acids Symp Ser,* 1978 (1), 185-188), was used in the synthesis of ribonucleosides as a reagent to selectively introduce protective groups into the 2'-OH position. Protecting a nucleoside by means of 1,3-dichloro-1,1,3,3-tetraisopropyldisiloxane first involves the reaction of the silyl chain with the primary 5 '-hydroxyl group. Since intramolecular reactions occur at high a speed, the other end of the silyl chain readily reacts with the closer secondary 3'-hydroxyl item of the same molecule, forming a seven-member ring. For spatial reasons, a reaction with the 2'-hydroxyl group is not possible. A characteristic feature of compounds protected with 1,3-dichloro-1,1,3,3-tetraisopropyldisiloxane is that compounds are formed as exemplified by the following formula:

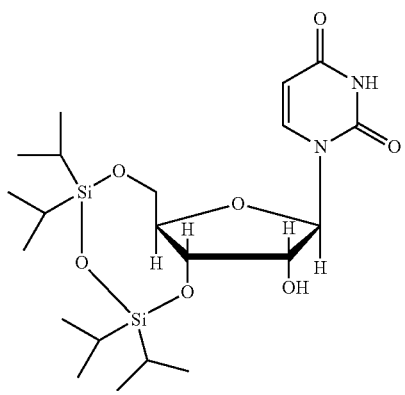

where the —Si—O—Si— disiloxane bond can be found. However, the high cost of obtaining 1,3-dichloro-1,1,3,3-tetraisopropyldisiloxane and the susceptibility of the tetraisopropyldisiloxane-1,3-diyl group to hydrolysis in a highly basic or acidic environment significantly limit the usability thereof, and additionally it is not possible to obtain the 2',3'-protected isomer in a direct reaction of ribonucleosides.

A publication by W. T.; Nowakowska, B.; Adrych, K. Tetra-t-butoxydisiloxane-1,3-diyl, a New Type of Bifunctional Silyl Protection Group. Nucleic Acids Research, symp. ser. 1987, 18, 149-152, describes a terta-t-butoxydisiloxane-1,3-diyl protecting agent. Using 1,3-dichloro-1,1,3,3-tetra-t-butoxysiloxane for protecting purposes leads the formation of compounds exemplified by the following formula:

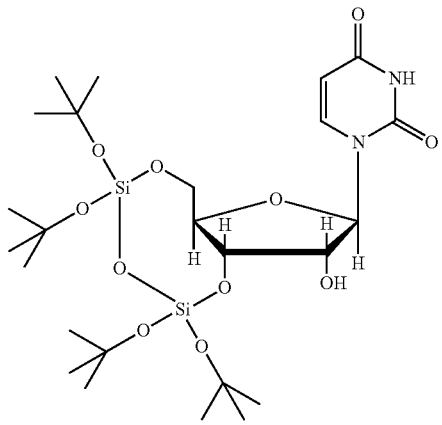

where the —Si—O—Si— disiloxane bond can also be found, but the presence of the t-butoxyl groups makes this protecting agent more durable in an acidic environment than the tetraisopropyldisiloxane-1,3-diyl agent, providing a wider range of applications. However, the use of the reagent is limited by its high cost. Additionally, it is not possible to obtain the 2',3'-protected isomer in a direct reaction of ribonucleosides.

In U.S. Pat. No. 6,800,751 presents bifunctional organosilicon protecting agents which have a group of atoms other than an oxygen atom between two silyl groups. An example of this type of protection is a protecting agent introduced by means of 1,2-dichloro-methylene-bis(diisopropylsilane), (MDPSCl$_2$), as exemplified by the compound of the following formula:

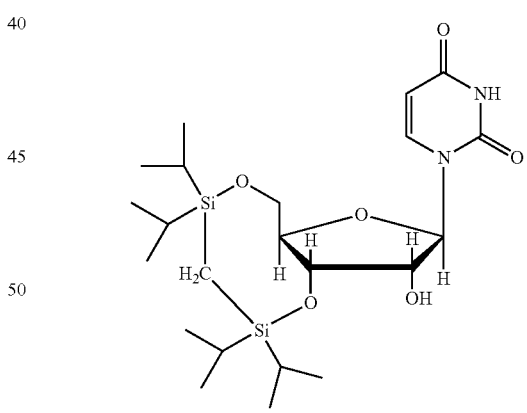

where the —Si—CH$_2$—Si-silylenmethylensilylen bond can be found.

This method found application in the regioselective alkylation of nucleosides, as was discussed by Wen, Ke, et al, in *The Journal of Organic Chemistry* 2002, 67 (22), 7887-7889. Expensive reagents are used in this method.

Also a silylen organosilicon protecting agent is also known from literature, comprising one silicon atom. This type of protection is exemplified by the compound with the di-tert-butylsilylen protecting agent of the following formula:

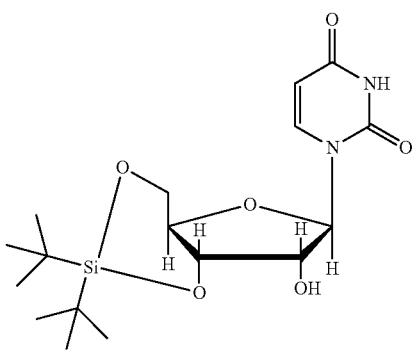

The di-tert-butylsilylen protecting agent introduced by means of the di-tert-butylsilyl bis(trifluoromethanesulfonate) reagent (DTBS) is often used to protect two hydroxyl items in nucleosides, as was discussed by E. J. Corey and P. B. Hopkins in *Tetrahedron Lett.*, 1982, 23, 4871, and to protect hydroxyl functions in the analysis of polyhydric alcohols by means of gas chromatography and mass spectrometry. A high cost of the reagent limits the application scope of this method. In the case of ribonucleosides, it is not possible to introduce a protecting group into positions 2' and 3'. When a protecting agent of this type is used in positions 3' and 5' of a nucleoside, the conformation of the protected compound is such that some reactions do not occur in the reaction centre. [K. Herbal, J. Kitteringham, M. Voyle, A. J. Whitehead, *Tetrahedron Letters*, 2005, 46, 2961-2964.]

The object of the invention is to improve the simultaneous protection of two hydroxyl, amine, or thiol functions, or one hydroxyl function and one amine function, or one amine function and one thiol function, and one hydroxyl function and one thiol function located at carbon atoms of different orders, particularly in sugars, polyalcohols, nucleosides, nucleotides, and nucleic acids, particularly in the reactions of an organic synthesis, as well as to provide novel compounds in the reaction of protecting reactive hydroxyl, amine, and thiol groups. Another object of the invention was to develop novel compounds useful in implementing the method of simultaneously protecting two functions.

According to the first aspect, the subject of the invention is the method of simultaneously protecting two hydroxyl, amine, or thiol functions, or one hydroxyl function and one amine function, or one hydroxyl function and one thiol function, or one thiol function and one amine function, consisting of protecting primary and secondary hydroxyl, amine, or thiol groups, particularly in sugars, polyalcohols, nucleosides, nucleotides, peptides, and nucleic acids in the reactions of an organic synthesis by carrying out a protecting reaction between a compound having at least two free hydroxyl, amine, or thiol groups, or at least one hydroxyl group and one amine group, or at least one hydroxyl group and one thiol group, or at least one amine group and one thiol group, and the disilane of formula 1,

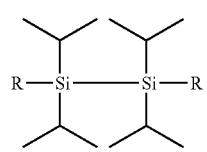

(1)

where R stands for Cl or Br, or I, or a substituent of formula 2,

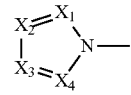

(2)

where $X_1$, $X_2$, $X_3$, $X_4$ are the same or different, and stand for N or CH, or the C—$R_1$ groups,
where $R_1$ are the same or different, and stand for:
a saturated alkyl containing 1 to 8 carbon atoms, preferably methyl;
an unsaturated alkyl containing 2 to 8 carbon atoms, preferably 2 carbon atoms;
an aryl, preferably phenyl or naphthyl, most preferably phenyl;
a substituted saturated alkyl containing 1 to 8 carbon atoms and an aryl substituent, preferably phenyl;
a substituted unsaturated alkyl containing 2 to 8 carbon atoms and an aryl substituent, preferably phenyl;
wherein, in each case, at least one X is different from N.

The protecting reaction is carried out in aprotic solvent, preferably selected from the group of solvents of aliphatic ethers, aliphatic nitriles, tertiary amides, aromatic bases, and the mixtures thereof, and most preferably selected from the group of pyridine, or tetrahydrofuran (THF), or acetonitrile, or N,N-dimethylformamide (DMF), or the mixtures thereof.

All of it is mixed, and when the reaction has been completed, the product is isolated from the post-reaction mixture by extraction.

The protecting reaction is carried out at a temperature of −55° C. to +50° C., the reaction temperature not being lower than the freezing point of the solvent. According to the invention, the process is preferably conducted at a room temperature. The time necessary for the completion of the protecting reaction depends on the temperature at which it is carried out, the type of the solvent used, the structure of reagents, as wells as the concentration of the reagents. In order to ensure an optimum process time, it is advisable to monitor the reaction using a thin-layer chromatography technique with silica gel on plates or the HPLC column chromatography.

Compounds obtained from this reaction have two hydroxyl groups, or two amine groups, or two thiol groups, or one hydroxyl group and one amine group, or one amine group and one thiol group, or one hydroxyl group and one thiol group simultaneously protected. The examples of such compounds with functional groups protected include the compounds of general formulas 6 and 7, where $R_2$ and B have the above meanings.

According to the invention, the method makes it possible to protect group pairs of the same type, namely hydroxyl, amine, or thiol groups, as well as any combination thereof. In particular, the method according to the invention is used to protect two hydroxyl group in organic compounds, such as sugars, polyalcohols, nucleotides or nucleic acid, and two amine groups especially in nucleosides. In addition to the simultaneous protecting of two hydroxyl groups in nucleosides the method may be used to protect one hydroxyl group and one amine group simultaneously.

The second variant of the method according the invention is the selective and simultaneous protection of two secondary hydroxyl, amine or thiol functions, or one hydroxyl function and one amine function, or one hydroxyl function and one thiol function, or one thiol function and one amine function, consisting of protecting hydroxyl, amine, or thiol groups, particularly in sugars, polyalcohols, nucleosides, nucleotides, peptides, and nucleic acids in the reactions of an organic synthesis, characterised in that the protecting reaction is carried out between a compound containing at least two free hydroxyl, amine, or thiol groups, or at least one hydroxyl group and one amine group, or at least one hydroxyl group and one thiol group, or at least one amine group and one thiol group, and the disilane of general formula 1, where R stands for Cl or Br or I, in aprotic solvent, preferably selected from a group of the solvents of aliphatic ethers, aliphatic nitriles, tertiary amides, aromatic bases, or the mixtures thereof, it being particularly preferable to use solvents from the group of pyridine or N,N-dimethylformamide (DMF), or a mixture of pyridine with THF or acetonitrile, wherein the volume fraction of pyridine is preferably not lower than 10%, or a mixture of DMF with acetonitrile or THF, wherein the volume fraction of DMF is preferably not lower than 10%, or a mixture of pyridine with DMF.

For example, the use of the compound of general formula 1, where R has the above meaning, in a reaction with a nucleoside in pyridine first of all leads to the selective protecting, in positions 2' and 3', of secondary hydroxyl, amine, or thiol groups, or one hydroxyl group and one amine group, or one amine group and thiol group in a molecule, wherein at least one primary group is unprotected. This makes it possible to carry out various types of reactions selectively, e.g. primary hydroxyl group acetylation. Selective acetylation of a nucleoside primary hydroxyl group would not be possible, since acetylation usually leads to the formation of a mixture of isomers which differ in location and the number of acetyl groups. After a silyl protecting group is removed and the reaction mixture purified, a nucleoside derivative with the primary hydroxyl group protected is used to obtain modified nucleosides, which finds practical application for example in diagnostics and DNA sequencing.

The third embodiment of the method according to the invention is the selective and simultaneous protection of two groups, i.e. one primary group (e.g. 5') and one secondary group (e.g. 3') of hydroxyl, amine, or thiol functions, or one hydroxyl function and one amine function, or one hydroxyl function and one thiol function, or one thiol function and one amine function, consisting of protecting hydroxyl, amine, or thiol groups, particularly in sugars, polyalcohols, nucleosides, nucleotides, peptides, nucleic acids during a protecting reaction between a compound containing at least two free hydroxyl, amine, or thiol groups, or one hydroxyl group and one amine group, or one thiol group and one amine group, or one hydroxyl group and one thiol group, and the disilane of general formula 1, where R stands for a substituent of formula 2,

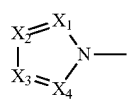

(2)

where $X_1$, $X_2$, $X_3$, $X_4$ are the same or different and stand for N or CH or the C—R1 groups where R1s are the same or different, and stand for:
  a saturated alkyl containing 1 to 8 carbon atoms, preferably methyl,
  an unsaturated alkyl containing 2 to 8 carbon atoms, preferably 2 carbon atoms,
  an aryl, preferably phenyl or naphthyl, most preferably phenyl,
  a substituted saturated alkyl containing 1 to 8 carbon atoms and an aryl substituent, preferably phenyl,
  a substituted unsaturated alkyl containing 2 to 8 carbon atoms and an aryl substituent, preferably phenyl,
  wherein, in each case, at least one X is different than N,
in aprotic solvent, selected from the group of solvents of aliphatic ethers, aliphatic nitriles, tertiary amides, aromatic bases, or the mixtures thereof, most preferably from the group of pyridine, or tetrahydrofuran (THF), or acetonitrile, or N,N-dimethylformamide (DMF), or the mixtures thereof. It is preferable to carry out the reaction in the presence a tertiary aliphatic amine. Preferably, triethylamine or diisopropylethylamine is used. The amount of a tertiary amine is not smaller than 0.05 of an equivalent weight in relation to the compound used of formula 1.

For the reaction, it is possible to use both pure disilane and disilane synthesised right before it is employed to protect a hydroxyl, amine, or thiol function. If disilane is not isolated, the amount a tertiary amine is not smaller than 2 equivalent weights in relation to silane so as to bind the hydrogen halide liberated in the reaction between the disilane halide of formula 1 and the respective compound of formula 3. Preferably, the amount of a tertiary amine is not smaller than 2.05 equivalent weights.

The method of this variant of the invention is used to protect any pair of a primary group and a secondary group of hydroxyl, amine, or thiol, which are located in relation to each other in such a way that a unit is produced as a result of protecting, constituting a 6-, 7-, or 8-member ring, including, amongst others, both protected groups and disilane bonds.

Selective protecting of one primary group and one secondary hydroxyl groups, for example widely used in ribonucleoside functionalisation processes carried out to introduce a protective group into 2' positions of ribonucleosides in synthesis of ribonucleic acid fragments (RNA), is of a great interest as it requires only two reactions instead of several successive reactions.

For example, the use of the compound of general formula 1, where R stands for the group of general formula 2, in the reaction with a nucleoside in a mixture of tetrahydrofuran and pyridine leads to the selective protecting of the primary hydroxyl group in position 5' and the secondary 3-hydroxyl group or an amine group, or one hydroxyl group and one amine group in a molecule, wherein the secondary group in position 2' is not protected and can be used in any reaction, e.g. in acetylation. In another embodiment, it is possible to carry out a protecting reaction of the group in position 2', and then to unprotect the groups in positions 5' and 3', and, using these groups, to conduct subsequent reactions, if this is required by the synthesis plan of the final product. The reactive functions of a molecule, such as hydroxyl, amine, or thiol groups, are protected, and consequently do not participate in the chemical transformation reaction, one that can successfully involve other unprotected functional centres. This makes it possible to carry out various types of reactions in a selective manner. For example, it would not be possible to acetylate a nucleoside selectively, since this would lead to the formation a mixture of isomers differing in location and the number of acetyl groups. After the silyl protecting group is removed and the reaction mixture purified, a nucleoside derivative with the secondary group protected is used to obtain modified nucleosides, which finds practical application for example in diagnostics and DNA sequencing.

Procedures of protecting of hydroxyl, amine or thiol groups are carried out according to the method of the invention and then known processes are employed to isolate the products. Most preferable is a process following the scheme below.

A disilane solution of general formula 1 or 8, alternatively including a tertiary amine, is added to a compound dissolved in an appropriate solution, containing not protected hydroxyl, amine or thiol groups. Disilane may be added as one portion or gradually. Preferably, it is added gradually. A different sequence of adding substrates is also possible, but may result in a different process yield.

Preferably, the course of the reaction is controlled by means of thin layer chromatography (TLC).

The reaction proceeds until the desired conversion level is achieved, when is ended by adding an aqueous solution of an alkalescent compound, preferably sodium or potassium bicarbonate. When the reaction has been ended, the excess of the solvent is removed and the product isolated, preferably by extraction into methylene chloride so that the reaction mixture can be preliminarily purified. It is permissible to carry out the extraction without initially removing the solvent.

The extract is dried, for example by means of anhydrous magnesium sulphate (VI), and then filtered, and afterwards the solvent is removed.

It is preferable to use an additive of a tertiary amine, but in case pure compounds of formula 1, where R stands for the group of formula 2, the amount of an amine is preferably not lower than 0.05 of an equivalent weight in relation to the disilane used, and in the case of a compound obtained right before the reaction together with the reaction mixture (a one-pot process), the amount of the amine used is not smaller than 2.05 equivalent weights. In the latter case, the triethylamine additive is intended to bind the hydrogen halide being formed, and the residue affects the course of the reaction. The excess of triethylamine can be easily removed by evaporation at a reduced pressure.

Column chromatography is used to purify the product, preferably using silica gel 60 of a particle size of 230-400 mesh and methanol in methylene chloride (1.0-5.0%) as an eluting phase.

The product may be also purified by means of HPLC.

An advantage of the invention is that it improves the simultaneous protection of two hydroxyl, amine, or thiol functions, or one hydroxyl function and one amine function, or one amine function and one thiol function, or one hydroxyl function and one thiol function located at carbon atoms of different orders.

The method of protecting two functions according the invention makes it possible to selectively carry out a reaction with unprotected reaction centres.

Known methods can be used to deprotect the hydroxyl, amine, or thiol groups protected by means of the method of the invention. A preferable, simple and effective method of removal of protection is to use fluorides, e.g. tetra-n-butylammonium or triethylammonium fluoride.

The second aspect of the invention includes novel compounds where there is a unit of general formula 4 or 5:

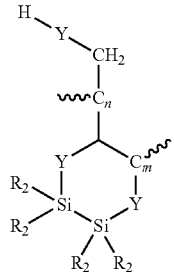

(4)

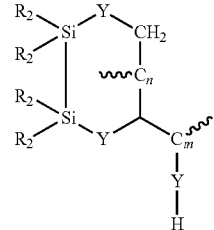

(5)

where
n has a value of 0 to 2
m has a value of 1 to 3
Ys are the same or different, and stand for NH or O, or S,
$R_2$s are the same or different, and stands for iPr or H.

Novel compounds are exemplified by the compounds of formula 6 or 7:

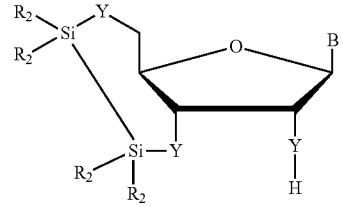

(6)

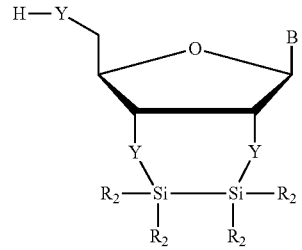

(7)

where $R_2$ and Y have the above meaning, and B stands for a heterocyclic residue of a nucleic base, also as protected, selected from the group comprising adenine, guanine, thymine, uracil, and cytosine.

Using the compound of general formula 1, where R has the above meaning according to the invention for simultaneously protecting two hydroxyl functions, two amine functions, or two thiol functions, or one hydroxyl function and one amine function, or one thiol function and one amine function, or one hydroxyl function and one thiol function makes it possible to protect them selectively, and consequently improves the selectiveness of a chemical reaction in a specific place of a molecule, while keeping intact another reactive part of this molecule.

The method of protecting hydroxyl and amine functions is of great significance to organic synthesis. Protecting hydroxyl and amine functions is especially useful in the chemical synthesis of sugars, polyalcohols, nucleosides, nucleotides, nucleic acids, which constitute a subject of extensive research and development activities on account of their application potential for medical diagnostics as well as for biology and biotechnology research.

It is the major application area of the method of protecting a hydroxyl or amine function, and of using novel compound for implementing this method that relates to the chemical synthesis of ribonucleic acid fragments (RNA), where structural units require simultaneous protection of positions 5' and 3' for a protecting group to be introduced selectively into position 2'.

The method may be particularly used in the chemical synthesis of ribonucleic acid (RNA) and in the chemical synthesis of modified nucleosides, as well as in medical diagnostics, and in research conducted by the departments of biology and biotechnology.

In the third aspect, the invention includes novel disilanes of general formula 1:

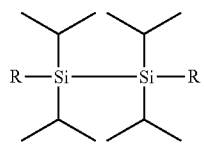

(1)

where R stands Br or I, or a substituent of formula 2,

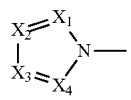

(2)

where $X_1$, $X_2$, $X_3$, $X_4$ are the same or different and stand for N or CH, or the C—R1 groups where R1s are the same or different and stand for:
- a saturated alkyl containing 1 to 8 carbon atoms, preferably methyl,
- an unsaturated alkyl containing 2 to 8 carbon atoms, preferably 2 carbon atoms,
- an aryl, preferably phenyl or naphthyl, most preferably phenyl,
- a substituted saturated alkyl containing 1 to 8 carbon atoms and an aryl substituent, preferably phenyl,
- a substituted unsaturated alkyl containing 2 to 8 carbon atoms and an aryl substituent, preferably phenyl,
  wherein, in each case, at least one X is different than N.

The disilanes of formula 1, where R stands for bromine or iodine, are obtained from the reaction between 1,1,2,2-tetraisopropyl-1,2-dihydrodisilane and dibromomethane or diiodomethane respectively in the presence of palladium chloride.

The disilanes of formula 1, where R stands for the group of formula 2, where $X_1$, $X_2$, $X_3$, $X_4$ have the above meaning, are obtained from the exchange reaction between 1,1,2,2-tetraisopropyl-1,2-dichlorodisilane and a respective compound of formula 3,

(3)

where $X_1$, $X_2$, $X_3$, $X_4$ have the above meaning, in a solvent in the presence of an aliphatic amine, preferably triethylamine, diisopropylethylamine as agents to bind hydrogen halide. The reaction is generally conducted for two hours, followed by isolation and purification by means of known methods. It is also possible to use the product of the reaction without having carried out the isolation and purification.

The invention is illustrated by the following examples.

EXAMPLE 1

1,2-dichloro-1,1,2,2-tetraisopropyldisilane 25 mmoles (5.71) g of 1,1,2,2-tetraisopropyl-1,2-dihydrosilane were placed in a flask 25, and a saturated solution of $Cl_2CH_2Cl_2$ was added drop by drop, with intensive mixing. Then, distillation was carried out under a 0.2 mm Hg vacuum. Fractions were collected at 122° C. The reaction produced 1,2-dichloro-1,1,2,2-tetraisopropyldisilane.

The yield of the reaction was 87.2%. The obtained product was transparent and slightly yellow liquid, which was later analysed by means of gas chromatography, GC (min) 16.22 (87.14%), gas chromatography combined with mass spectrometry, GC-MS (m/z): 221.30, 263.00, and nuclear magnetic resonance spectrometry.

$^1$H NMR (400 MHz, $C_6D_6$) δ (ppm): 1.22 (m, 24H), 1.35 (m, 4H), $^{13}$C NMR (100 MHz, $C_6D_6$) δ (ppm): 18.10, 17.79, 16.74.

$^{29}$Si NMR (79.5 MHz, $C_6D_6$) δ (ppm): 24.67

EXAMPLE 2

Protecting a Hydroxyl Group 0.25 mmole (60 mg) of uridine was placed in a flask and 2 mL of pyridine added. Next, 0.325 mmole (97.2 mg) of the 1,2-dichloro-1,1,2,2-tetraisopropyldisilane obtained according to example 1 was added, dissolved in 0.5 mL of pyridine. All of it was mixed. The reaction was ended after 60 minutes, and 6 mL of an aqueous saturated solution of sodium bicarbonate and 6 mL of methylene chloride were added. Afterwards, the organic layer was collected and dried with anhydrous sodium sulphate for approximately 30 minutes. The reaction mixture was applied onto a chromatography column. Containing the reaction product, (2'-3'-O-(tetraisopropyldisilane-1,2-diyl)uridine), the isolated fractions were combined and lyophilised.

The product, 2',3'-O-(tetraisopropyldisilane-1,2-diyl)uridine, was obtained from the reaction with secondary hydroxyl groups protected. With a yield of 95%, 114 mg of 2%3'41)-(tetraisopropyldisilane-1,2-diyl)uridine were obtained as white powder.

The compound was characterised by means of a nuclear magnetic resonance analysis.

$^1$H NMR (400 MHz, $CDCl_3$) δ (ppm): 8.62 (s, 1H), 7.62 (d, J=8 Hz, 1H), 5.72 (d, J=8 Hz, 1H), 5.67 (d, J=4.8 Hz, 1H), 4.52 (t, J=4.4 Hz, 1H), 4.35 (t, J=4.8, 1H), 4.15 (m, 1H), 3.97 (m, 1H), 3.79 (m, 1H), 1.35-1.03 (m, 28H), $^{13}$C NMR (100 MHz, CDCl$_3$) δ (ppm): 163.05, 150.06, 141.76, 102.15, 93.29, 85.54, 75.20, 71.63, 61.69, 17.54, 15.17, 15.13, 14.18, 14.01, $^{29}$Si NMR (79.5 MHz, CDCl$_3$) δ (ppm): 14.02; 13.37.

EXAMPLES 3-9

As with example 2, examples 3-9 were carried out; solvent compositions and the type of groups protected are presented in table 1.

TABLE 1

| Nn. | Solvent | Protected positions | Yield [%] |
|---|---|---|---|
| 3 | DMF | 2'-3' | 90 |
| 4 | THF | — | — |
| 5 | DMF + THF | 2'-3' | 75 |
| 6 | Pyridine + THF | 2'-3' | 80 |
| 7 | Acetonitrile | — | — |
| 8 | Acetonitrile + DMF | 2'-3' | 85 |
| 9 | Acetonitrile + Pyridine | 2'-3' | 70 |

EXAMPLE 10

Acetylation of 2',3'-O-(tetraisopropyldisilane-1,2-diyl)uridine 0.053 mmole (25 mg) of 2',3'-O-(tetraisopropyldisilane-1,2-diyl)uridine, 2.1 mmoles (0.200 mL) of acetic anhydride and 1 mL of pyridine were put in a flask. After 30 minutes the reaction was stopped by evaporating the reaction mixture with a mixture of methanol and toluene. The reaction mixture was applied onto a chromatography column. The isolated 345 fractions were combined and lyophilised. With a yield of 98%, 26 mg of 5'-O-acetyl-2',3'-O-(tetraisopropyldisilane-1,2-diyl)uridine were obtained. The reaction product was characterised by means of spectra.

$^1$H NMR (400 MHz, CDCl$_3$) δ (ppm): 8.22 (s, 1H), 7.56 (d, J=8.4 Hz, 1H), 5.82 (d, J=2.4 Hz, 1H), 5.72 (dd, J=2 Hz, 1H), 4.37-4.30 (m, 3H), 4.28-4.25 (m, 1H), 4.15 (m, 1H), 2.12 (s, 3H), 1.34-1.07 (m, 28H), $^{13}$C NMR (100 MHz, CDCl$_3$) δ (ppm): 170.35, 162.65, 149.69, 139.56, 102.02, 91.61, 81.55, 75.76, 71.88, 63, 25, 20.82, 15.52, 14.84, 14.15, 14.07, $^{29}$Si NMR (79.5 MHz, CDCl$_3$) δ (ppm): 16.03, 12.24.

The acetylating reaction proves the presence of a free hydroxyl group in the 5'-hydroxyl position of nucleotides. After removing the silyl protecting agent from 5'-O-acetylo-2',3'-O-(tetraisopropyldisilane-1,2-diyl)uridine using 0.084 mmole (22 mg) of tetra-n-butylammonium fluoride within 30 minutes, the reaction was ended by adding 6 ml of sodium bicarbonate and 6 ml of methylene chloride. The organic layer was collected and dried with anhydrous sodium sulphate for 30 minutes. Onto a chromatography column was applied the reaction mixture. The isolated fractions containing the deprotection product (5'-O-acetyluridine) were combined and lyophilised. A nuclear magnetic resonance spectrometry analysis confirmed that 5'-O-acetyluridine had been obtained.

EXAMPLE 11

1,2-di(imidazol-1-yl)-1,1,2,2-tetraisopropyldisilane 1 mL of tetrahydrofuran was placed in a flask, and 0.845 mmole (57.5 mg) of imidazole was added. Next, 0.325 mmole (97.2 mg) of 1,2-dichloro-1,1,2,2-tetraisopropyldisilane obtained according to example 1 was added. Afterwards, 1.625 mmoles (164.4 mg, 0.226 mL) of triethylamine (C$_2$H$_5$)$_3$N were added to the mixture, and it was mixed for 2 hours.

The product of the reaction was 1,2-di(imidazole-1-yl)-1,1,2,2-tetraisopropyldisilane, which was characterised without having been isolated by means of nuclear magnetic resonance spectrometry.

$^1$H NMR (400 MHz, CDCl$_3$) δ (ppm): 7.63 (s, 2H), 7.05 (s, 4H), 0.97-1.07 (m, 28H)

$^{13}$C NMR (100 MHz, CDCl$_3$) δ (ppm): 139.65, 129.75, 120.62, 18.11, 17.79, 16.74, $^{29}$Si NMR (79.5 MHz, CDCl$_3$) δ (ppm): 15.47.

EXAMPLE 12

A solution of 0.25 mmole of uridine (60 mg) in 1 mL of pyridine was added to the post-reaction mixture of example 11 containing 0.325 mmole (117.7 mg) of 1,2-di(imidazole-1-yl)-1,1,2,2-tetraisopropyldisilane. The solution contained a residue of 0.975 mole of the unbounded triethylamine. Then, all of it was mixed, and after 90 minutes a saturated hydrous solution of 6 mL of sodium bicarbonate and 6 mL of methylene chloride was added to end the reaction. Next, the organic layer was collected and dried with anhydrous sodium sulphate for 30 minutes. The reaction mixture was applied onto a chromatography column. The isolated fractions containing the reaction product were combined and lyophilised.

As a result of the reaction, 3',5'-O-(tetraisopropylodisilane-1,2-diyl)uridine was obtained, with primary and secondary hydroxyl groups protected. With a yield of 90%, 110 mg of 3',5'-O-(tetraisopropylodisilane-1,2-diyl)uridine were produced as white powder. The compound was characterised by means of nuclear magnetic resonance spectrometry.

$^1$H NMR (400 MHz, CDCl$_3$) δ (ppm): 9.34 (s, 1H), 7.24 (d, J=8 Hz, 1H), 5.71 (d, J=8 Hz, 1H), 5.48 (s, 1H), 4.51 (t, J=7 Hz, 1H), 4.37 (d, J=6 Hz, 1H), 4.14 (dd, J=3.6 Hz, 1H), 4.01 (dd, J=3.6 Hz, 1H), 3.81 (dd, J=9.2, 1H), 3.46 (s, 1H), 1.41-1.02 (m, 28H)

$^{13}$C NMR (100 MHz, CDCl$_3$) δ (ppm): 163.51, 149.66, 142.20, 102.21, 94.85, 83.23, 75.76, 75.02, 64.96, 17.96, 17.01, 15.25, 14.64, $^{29}$Si NMR (79.5 MHz, CDCl$_3$) δ (ppm): 18.29, 17.06.

EXAMPLES 13-26

As with example 12, examples 13-26 were carried out; table 2 presents the composition of solvents, the presence or lack of triethylamine (Et$_3$N), and the type of the protected groups.

TABLE 2

| No. | Solvent | Et$_3$N [mmole] | Protected positions | Yield [%] |
|---|---|---|---|---|
| 13 | DMF | 0 | 3'-5' | 40 |
|  |  |  | 2'-3' | 30 |
| 14 | DMF | 0.975 | 3'-5' | 85 |
|  |  |  | 2'-3' | 10 |
| 15 | THF | — | 2'-3' | 70 |
| 16 | THF | 0.975 | 3'-5' | 60 |
|  |  |  | 2'-3' | 25 |
| 17 | Acetonitrile | 0 | 3'-5' | 50 |
|  |  |  | 2'-3' | 30 |
| 18 | Pyridine | 0 | 2'-3' | 75 |
| 19 | Pyridine | 0.975 | 3'-5' | 85 |
| 20 | THF + DMF | 0 | 3'-5' | 60 |
|  |  |  | 2'-3' | 30 |

TABLE 2-continued

| No. | Solvent | Et$_3$N [mmole] | Protected positions | Yield [%] |
|---|---|---|---|---|
| 21 | THF + DMF | 0.975 | 3'-5' | 90 |
|    |           |       | 2'-3' | 5 |
| 22 | THF + Pyridine | 0 | 2'-3' | 75 |
| 23 | Acetonitrile + DMF | 0 | 3'-5' | 50 |
|    |                    |   | 2'-3' | 30 |
| 24 | Acetonitrile + DMF | 0.975 | 3'-5' | 70 |
|    |                    |       | 2'-3' | 15 |
| 25 | Acetonitrile + Pyridine | 0 | 3'-5' | 55 |
|    |                         |   | 2'-3' | 25 |
| 26 | Acetonitrile + Pyridine | 0.975 | 3'-5' | 85 |
|    |                         |       | 2'-3' | 10 |

EXAMPLE 27

0.053 mmole (25 mg) of 3',5'-O-(tetraisopropyldisilane-1,2-diyl)uridine, 2.1 mmoles (0.200 mL) of acetic anhydride, and 1 mL of pyridine were put into a flask. After 30 minutes the reaction was ended by evaporating the reaction mixture with a mixture of methanol and toluene. The reaction mixture was applied onto a chromatography column. After being combined, the isolated fractions were lyophilised. With a yield of 100%, 27 mg of 2'-O-acetyl-3',5'-O-(tetraisopropyldisilane-1,2-diyl)uridine were obtained. The reaction product was characterized by means of a spectrum.

$^1$H NMR (400 MHz, CDCl$_3$) δ (ppm): 8.57 (s, 1H), 7.23 (d, J=8 Hz, 1H), 5.74 (d, J=8.4 Hz, 1H), 5.69 (d, J=2 Hz, 1H), 5.48 (dd, J=2 Hz, J=4.4 Hz, 1H), 4.41 (dd, J=6.8 Hz, J=1.6 Hz, 1H), 4.15 (dd, J=3.6 Hz, J=8.4 Hz, 1H), 4.00 (m, 1H), 3.85 (dd, J=7.6 Hz, J=4.4 Hz, 1H), 2.13 (s, 3H), 1.36-1.04 (m, 28H), $^{13}$C NMR (100 MHz, CDCl$_3$) δ (ppm): 169.26, 162.47, 149.41, 140.42, 102.71, 90.29, 83.03, 75.69, 74.63, 64.63, 20.67, 18.35, 17.51, 15.26, 14.89, $^{29}$Si NMR (79.5 MHz, CDCl$_3$) δ (ppm): 18.52, 17.03.

The acetylating reaction proves the presence of a free group in hydroxyl position 2' of nucleosides. After removing the silyl protecting group from 2'-O-acetyl-3',5'-O-(tetraisopropyldisilane-1,2-diyl)uridine by means of 0.088 mmole (23 mg) of tetra-n-butylammonium fluoride within 30 minutes, the reaction was ended by adding 6 ml of sodium 420 bicarbonate and 6 ml of methylene chloride. The organic layer was collected and dried with anhydrous sodium sulphate for 30 minutes. The reaction mixture was applied onto a chromatography column. After being combined, the isolated fractions containing the product of the unprotecting, 2'-O-acetyluridine, were lyophilized. The analysis made by means of nuclear magnetic resonance spectrometry proved that 2'-O-acetyluridine had been obtained.

EXAMPLE 28

Protecting a Hydroxyl Group and Amine Group 0.40 mmole (100 mg) of 3'-amino-2',3'-dideoxyadenosine was put in a flask, and 1 mL of pyridine was added. Then, 0.52 mmole (155.5 mg, 0.159 mL) of 1,2-dichloro-1,1,2,2-tetraisopropyldisilane was added after being obtained according to example 1 and dissolved in 0.5 mL of pyridine. All of it was mixed and after 60 minutes 6 mL of a hydrous saturated solution of bicarbonate sodium and 6 ml of methylene chloride were added. The organic layer was collected and dried with anhydrous sodium sulphate for 30 minutes. The reaction mixture was applied onto a chromatography column. After being combined, the isolated fractions containing the reaction product were lyophilized.

With a yield of 85%, 162 mg of 3'-amino-3'-N-5'-O-(tetraisopropyldisilane-1,2-diyl)-2',3'-dideoxyadenosine were obtained as white powder.

The compound was characterized on the basis of a nuclear magnetic resonance analysis.

As result of the reaction, 3'-amino-3'-N-5'-O-(tetraisopropyldisilane-1,2-diyl)-2',3'-dideoxyadenosione was obtained, with the primary hydroxyl group and amine group protected.

$^1$H NMR (400 MHz, DMSO) δ (ppm): 8.23 (s, 1H), 8.10 (s, 1H), 7.23 (s, 214), 6.30 (q, J=4.4 Hz, J=6.8 Hz, 1H), 5.11 (s, 1H), 3.90 (m, 1H), 3.78 (m, 1H), 3.69 (m, 2H), 2.71-2.61 (m, 1H), 2.25-2.18 (m, 1H), 1.12-0.92 (m, 28H), $^{13}$C NMR (125.8 MHz, DMSO) δ (ppm): 155.95, 152.40, 148.85, 138.95, 128.28, 87.49, 82.97, 64.43, 51.67, 39.65, 18.00, 17.84, 15.56, 14.50, $^{29}$Si NMR (79.5 MHz, DMSO) δ (ppm): 15.72; 10.92.

EXAMPLE 29

1,2-dibromo-1,1,2,2-tetraisopropyldisilane 0.66 mmole of 1,1,2,2-tetraisopropyl-1,2-dihydrosilane (151.8 mg, 0.180 mL), 0.03 mmole of palladium chloride (8 mg, 4.5 mol %) and 14.3 mmoles of dibromomethane (2477 mg, 1000 mL) were put in a flask. Then, all of it was mixed for 4 h at a temperature of 60° C.

1,2-dibromo-1,1,2,2-tetraisopropyldisilane was obtained as a product, which was characterised by means of nuclear magnetic resonance spectrometry without being isolated.

$^{29}$Si NMR (99.4 MHz, C$_6$D$_6$) δ (ppm): 39.89 ppm.

EXAMPLE 30

Protecting a Hydroxyl Group 0.5 mL of pyridine was added to 1,2-dibromo-1,1,2,2-tetraisopropyldisilane of general formula 1 that was newly obtained according to example 30. Next, a mixture of 0.615 mmole of uridine (150 mg) in pyridine was added Then, it was heated to a room temperature and mixed for 1 hour. After that time, in order to end the reaction, 6 mL of a saturated hydrous solution of sodium bicarbonate and 6 mL of methylene chloride were added. Next, the organic layer was collected and dried with anhydrous sodium sulphate for 30 minutes. The reaction mixture was applied onto a chromatography column. After being combined, the isolated fractions containing the reaction product were lyophilized.

With a yield of 80%, 191 mg of 2'-3'-O-(tetraisopropyldisilane-1,2-diyl)uridine were obtained as white powder. The secondary hydroxyl groups of the reaction product were protected.

The compound was characterised on the basis of a nuclear magnetic resonance analysis.

$^1$H NMR (400 MHz, CDCl3) δ (ppm): 8.62 (s, 1H), 7.62 (d, J=8 Hz, 1H), 5.72 (d, J=8 Hz, 1H), 5.67 (d, J=4.8 Hz, 1H), 4.52 (t, J=4.4 Hz, 1H), 4.35 (t, J=4.8, 1H), 4.15 (m, 1H), 3.97 (m, 1H), 3.79 (m, 1H), 1.35-1.03 (m, 28H), $^{13}$C NMR (100 MHz, CDCl3) δ (ppm): 163.05, 150.06, 141.76, 102.15, 93.29, 85.54, 75.20, 71.63, 61.69, 17.54, 15.17, 15.13, 14.18, 14.01, 29Si NMR (79.5 MHz, CDCl3) δ (ppm): 14.02; 13.37.

In order prove that 2',3'-O-(tetraisopropyldisilane-1,2-diyl)uridine had been obtained, it was acetylated as in example 10. Afterwards, 5'-O-acetyl-2',3'-O-(tetraisopropyldisilane-1,2- diyl)uridine was unsilylated by means of 0.084 mmole (22 mg) of tetra-n-butylammonium fluoride within 30 minutes. In order to end the reaction, 6 mL of sodium bicarbonate and 6 mL of methylene chloride were added. Having been collected, the organic layer was dried with anhydrous sodium sulphate for 30 minutes. The reaction mixture was applied onto a chromatography column. After being combined, the isolated fractions containing the product, 5'-O-acetyluridine, were lyophilized. An analysis using nuclear magnetic resonance spectrometry proved that 5'-O-acetyluridine had been obtained.

EXAMPLES 31-37

As with example 30, examples 31-37 were carried out. Table 3 presents the composition of solvents and the type of groups protected.

TABLE 3

| No. | Solvent | Protected positions | Yield [%] |
| --- | --- | --- | --- |
| 31 | DMF | 2'-3' | 80 |
| 32 | THF | — | — |
| 33 | DMF + THF | 2'-3' | 65 |
| 34 | Pyridine + THF | 2'-3' | 70 |
| 35 | Acetonitrile | — | — |
| 36 | Acetonitrile + DMF | 2'-3' | 75 |
| 37 | Acetonitrile + Pyridine | 2'-3' | 60 |

EXAMPLE 38

Unprotecting Hydroxyl Groups 0.127 (60 mg) mmole of 3',5'-O-(tetraisopropyldisilane-1,2-diyl)uridine was put in a flask, and 1 mL of tetrahydrofuran was added. Afterwards, 0.191 mmole (50 mg) of tetra-n-butylammonium fluoride was added. After three hours the reaction was ended by adding a reagent to stop the process in the form of 6 ml of sodium bicarbonate and 6 mL of methylene chloride. Having been collected, the organic layer was dried with anhydrous sodium sulphate for 30 minutes. The reaction mixture was applied onto a chromatography column. After being combined, the isolated fractions containing the unprotecting product, uridine, were lyophilized. The compound was characterized by means of nuclear magnetic resonance spectrometry.

The NMR analysis proved that the compound obtained by removing the protecting group was uridine. In the process of protecting hydroxyl functions, the structure of nucleosides was not changed by introducing or removing a silyl protecting group.

The invention claimed is:

1. A method of simultaneously protecting two hydroxyl, amine, or thiol functions, or one hydroxyl and one amine function, or one hydroxyl and one thiol function, or one thiol and one amine function, comprising protecting primary and secondary hydroxyl, amine, or thiol groups, wherein a compound containing at least two free hydroxyl, amine, or thiol groups, or at least one hydroxyl group and one amine group, or at least one hydroxyl group and one thiol group, or at least one amine group and one thiol group is made to react with a compound of general formula 1,

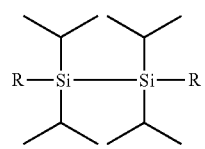

(1)

where R stands for Cl or Br or I, or a substituent of formula 2,

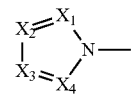

(2)

where $X_1, X_2, X_3, X_4$ are the same or different and stand for N or CH, or C—$R_1$ groups, where $R_1$s are the same or different, and stand for:
 a saturated alkyl containing 1 to 8 carbon atoms,
 an unsaturated alkyl containing 2 to 8 carbon atoms,
 an aryl;
 a substituted saturated alkyl containing 1 to 8 carbon atoms and an aryl substituent,
 a substituted unsaturated alkyl containing 2 to 8 carbon atoms and an aryl substituent;
 wherein, in each case, at least one X is different from N, in the environment of an aprotic solvent.

2. The method according to claim 1 wherein compounds are used in which the $X_1, X_2, X_3, X_4$ substituents are the same or different and where $R_1$s are the same or different and stand for methyl, an unsaturated alkyl containing 2 carbon atoms, phenyl, naphthyl, a phenyl-substituted saturated alkyl containing 1 to 8 carbon atoms, or a phenyl-substituted unsaturated alkyl containing 2 to 8 carbon atoms.

3. The method according to claim 1 wherein the reaction is carried out in the environment of a solvent selected from the group of aliphatic ethers, aliphatic nitriles, tertiary amides, aromatic bases, and mixtures thereof.

4. The method according to claim 1 wherein the reaction is carried out in the environment of a solvent selected from the group of pyridine, tetrahydrofuran, acetonitrile, N,N-dimethylformamide, and mixtures thereof.

5. A method of selectively and simultaneously protecting two secondary hydroxyl, amine or thiol functions, or one hydroxyl and one amine function, or one hydroxyl and one thiol function, or one thiol and one amine function, comprising protecting secondary hydroxyl, amine or thiol groups, wherein a compound containing at least two free hydroxyl or amine or thiol groups, or at least one hydroxyl group and one amine group, or at least one hydroxyl group and one thiol group, or at least one amine group and one thiol group is made to react with a compound of general formula 1,

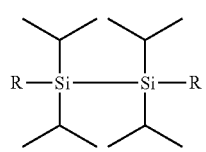

(1)

where R stands for Cl or Br or I, in the presence of an aprotic solvent.

6. The method according to claim 5 wherein the reaction is carried out in the environment of a solvent selected from the group of aliphatic ethers, aliphatic nitriles, tertiary amides, aromatic bases and mixtures thereof.

7. The method according to claim 6 wherein the reaction is carried out in the environment of a solvent selected from the group of pyridine, tetrahydrofuran, acetonitrile, N,N-dimethylformamide, and mixtures thereof.

8. The method according to claim 7 wherein the reaction is carried out in the environment of a solvent selected from the group of a mixture of pyridine with tetrahydrofuran or acetonitrile, and a mixture of N,N-dimethylformamide with acetonitrile or tetrahydrofuran.

9. The method according to claim 8 wherein the reaction is carried out in the environment of a solvent selected from the group of a mixture of pyridine with tetrahydrofuran or acetonitrile wherein the volume fraction of pyridine is not smaller than 10%, and a mixture of N,N-dimethylformamide with acetonitrile or tetrahydrofuran wherein the volume fraction of N,N-dimethylformamide is not smaller than 10%.

10. A method of selectively and simultaneously protecting two—one being primary and the other secondary—hydroxyl or amine or thiol functions, or one hydroxyl and one amine function, or one hydroxyl and one thiol function, or one thiol and one amine function, comprising protecting primary and secondary hydroxyl, amine or thiol groups, wherein a compound containing at least two free hydroxyl or amine or thiol groups, or at least one hydroxyl group and one amine group, or at least one hydroxyl group and one thiol group, or at least one amine group and one thiol group is made to react with a compound of general formula 1,

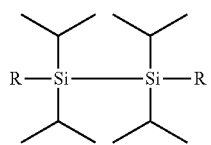

R stands for a substituent of formula 2,

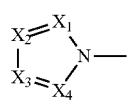

where $X_1, X_2, X_3, X_4$ are the same or different and stand for N or CH, or C—$R_1$ groups,
where $R_1$s are the same or different, and stand for:
  a saturated alkyl containing 1 to 8 carbon atoms;
  an unsaturated alkyl containing 2 to 8 carbon atoms;
  an aryl;
  a substituted saturated alkyl containing 1 to 8 carbon atoms and an aryl substituent;
  a substituted unsaturated alkyl containing 2 to 8 carbon atoms and an aryl substituent;
  wherein, in each case, at least one X is different from N,
  in an aprotic solvent and, optionally, in the presence of a tertiary aliphatic amine.

11. The method according to claim 10 wherein compounds are used in which the $X_1, X_2, X_3, X_4$ substituents are the same or different and where $R_1$s are the same or different and stand for methyl, an unsaturated alkyl containing 2 carbon atoms, phenyl, naphthyl, a phenyl-substituted saturated alkyl containing 1 to 8 carbon atoms, and a phenyl-substituted unsaturated alkyl containing 2 to 8 carbon atoms.

12. The method according claim 10 wherein the reaction is carried out in the environment of a solvent selected from the group of aliphatic ethers, aliphatic nitriles, tertiary amides, aromatic bases, and mixtures thereof.

13. The method according to claim 10 wherein the reaction is carried out in the environment of a solvent selected from the group of pyridine, tetrahydrofuran, acetonitrile, N,N-dimethylformamide, and mixtures thereof.

14. The method according to claim 10 wherein the tertiary amine is present and the amount thereof is not smaller than 0.05 of an equivalent weight in relation to the disilane used.

15. The method according to claim 10 wherein the tertiary amine is present and is triethylamine or diisopropylethylamine.

16. A compound of general formula 1,

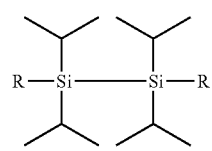

where R stands for a substituent of formula 2,

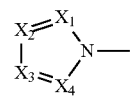

where $X_1; X_2, X_3, X_4$ are the same or different and stand for N or CH, or C—$R_1$ groups,
where $R_1$s are the same or different, and stand for:
  a saturated alkyl containing 1 to 8 carbon atoms;
  an unsaturated alkyl containing 2 to 8 carbon atoms;
  an aryl;
  a substituted saturated alkyl containing 1 to 8 carbon atoms and an aryl substituent;
  a substituted unsaturated alkyl containing 2 to 8 carbon atoms and an aryl substituent;
  wherein, in each case, at least one X is different from N.

17. A compound of general formula 6 or 7:

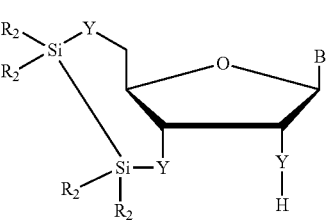

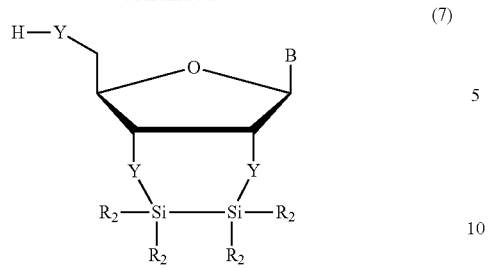 (7)
where
Ys are the same or different, and stand for NH, O or S,
$R_2$s are the same or different, and stand for iPr or H, and
B stands for a heterocyclic residue of a nucleic base selected from the group of adenine, guanine, thymine, uracil, and cytosine.
* * * * *